United States Patent

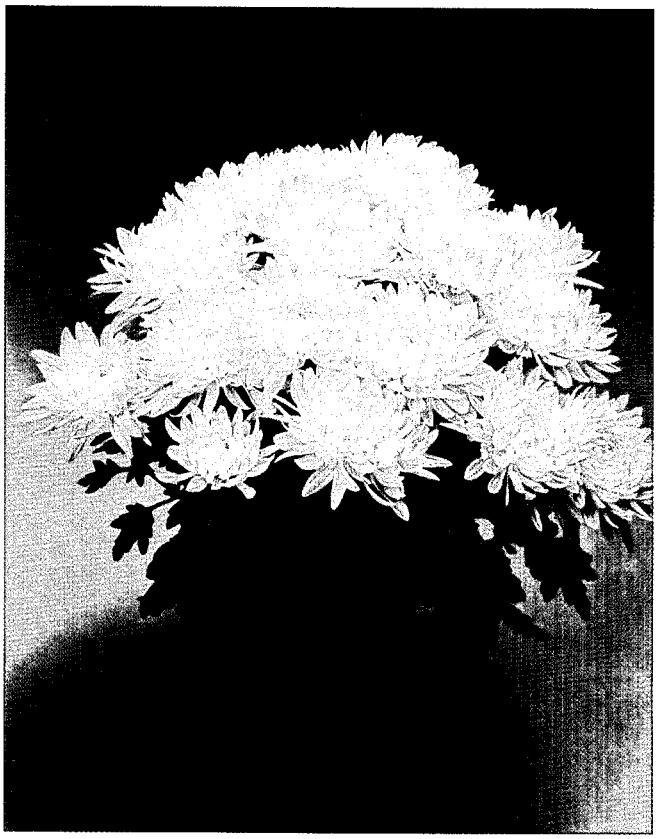
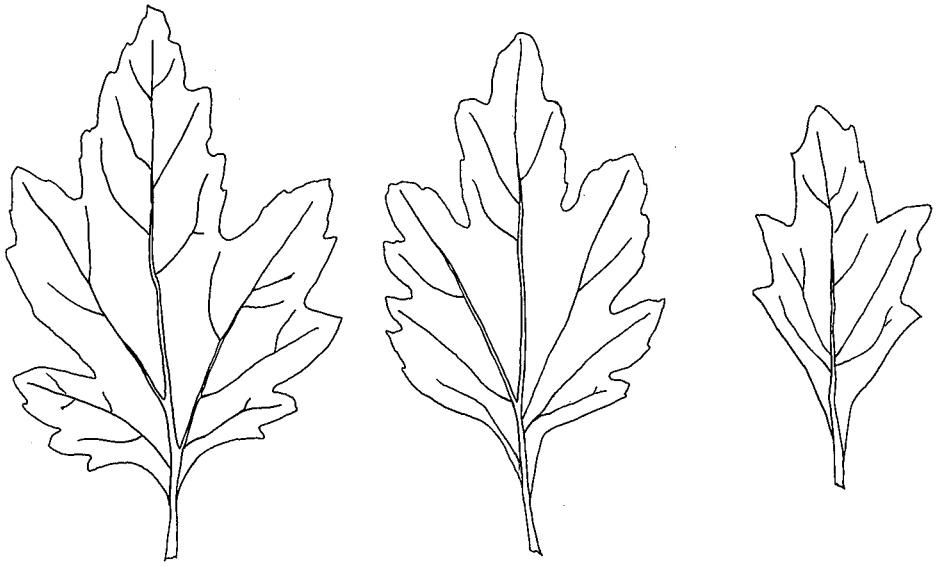

Plant Pat. 3,812

Patented Dec. 2, 1975

3,812

CHRYSANTHEMUM (INDEPENDENCE)

Leonard H. Shoesmith, Westfield, Woking, Surrey, England, assignor to Pan-American Plant Company, West Chicago, Ill.

Filed Nov. 4, 1974, Ser. No. 520,427

Int. Cl. A01h 5/00

U.S. Cl. Plt.—77 1 Claim

ABSTRACT OF THE DISCLOSURE

A new variety of chrysanthemum of the greenhouse pot plant category characterized by the pure white color of its very large semi-incurve flower form, its excellent keeping qualities and its resistance to pinking under low light conditions.

BACKGROUND OF THE NEW PLANT

This new chrysanthemum plant was discovered by me in 1970 among random pollinated plants grown in greenhouse at West Chicago, Ill., as part of a program directed to the developing of new and improved varieties suitable for commercial exploitation. The very large size of the pure white blooms of this plant caused me to select it for propagation and test and this was done under my direction at West Chicago, Ill., by means of cuttings from the original plant. Subsequent propagation of this plant by vegetative cuttings and through many generations, at West Chicago, Ill., and at Cortez, Fla., has demonstrated that the distinctive characteristics of the plant hold true from generation to generation and thus appear to be firmly fixed.

DESCRIPTION OF THE DRAWING

This new variety of chrysanthemum is illustrated by the accompanying full color photographic drawing which shows the flower form and color characteristics of the plant; and which shows the distinctive configuration of the leaves by means of pen and ink drawings, the drawings being of leaves taken at several stages of maturity.

DESCRIPTION OF THE NEW PLANT

The following is a detailed description of my new chrysanthemum plant with color designations made according to the Horticultural Colour Chart, by Robert F. Wilson, published by The Royal Horticultural Society of London, England.

*The plant*

Origin: Seedling.
Parentage: Unidentified.
Classification:
- Botanic—*Chrysanthemum morifolium.*
- Commercial—Greenhouse pot plant.

Form: Perennial herbaceous bush.
Height: 13 inches.
Growth: Terminal, upright and vigorous.
Branching: Normal, fairly strong and of medium sturdiness.
Foliage: Quantiy—about 8 leaves per stem.
- Leaf size: Mature—4 inches long x 2½ inches wide. Younger leaves are smaller.
- Leaf shape: Lobed—ovate.
- Venation: Pinnately veined.
- Color: Upper side—Parsley Green 00962. Under side—Spinach Green 0960/3.
- Surface texture: Canescent.
- Petioles: About 1 inch long.

*The bud*

Form: Almost flat.
Size: Large—¾ inch in diameter, ⅜ inch deep.
Opening rate: Bud opens slowly.
Color: When phyllaries divide—Lettuce Green 861/2. When florets begin to unfurl—Primrose Yellow 601/3.
Phyllaries: The outside of the receptacle bears many distinct involucral upstanding bracts.
- Color: Inside—Spinach Green 0960/2. Outside—Spinach Green 0960/1.
- Surface texture: Canescent.
- Peduncle: Erect. About 1¼ to 1¾ inches long.
- Surface texture: Canescet.

*The flower*

Flowering capability: This plant can be flowered the year around with photoperiod control.
- Response: 10 week.
- Recommended flowering: October to May.
- Natural season flowering: About November 5.
- Blooms:
- Flower type: Semi-incurve.
- Borne: Singly when disbudded, in multiples when grown as a spray plant.

Size: Very large.
- Diameter: 4½ to 5¾ inches.
- Depth: About 1¼ inches.

Shape: Cup shaped when bloom first opens. Bloom opens up as it matures with a slight reflexing of the lower petals.
Florets: Number—Many ray florets.
- Form: Composite. Mostly ray petals which have a lineal shape with generally obtuse apex. The tips of many petals have a slight cuspidate projection and occasionally some outer petals will be spooned.
- Color: All florets are white on both upper and under sides. Immature florets are yellow at their base or inner ends and this color fades to white as the bloom matures.
- Texture: Medium firm.
- Aspect: Velvety.
- Discoloration: This flower does not pink.

Peduncle: Upright and of medium sturdiness.
- Length: 1¼ to 1¾ inches.
- Color: Scheeles Green 860.

Persistence: Petals hang on and dry.
Fragrance: Slight.
Lasting quality: 3 weeks on plant. This is not recommended for cut flowers and is recommended only for greenhouse culture.

*Reproducitve Organs*

Stamens: Arrangement—5 syngenesious stamens, connate by their anthers to form a cylinder about the style.
- Filaments: Length—1/16 inch.
  - Color: Light yellow.
- Pollen: Color—Yellow.

Pistils: Number—One to each ray floret.
- Length: ⅛ inch.
- Stigmas: Color—Yellow.

Ovaries: Inferior and bicarpellate.

This plant is distinguished by the very large size and the pure white color of its blooms and by its resistance to pinking under low temperatures. The blooms are of a semi-incurve flower from, with slight reflexing of the outer petals under low light conditions, and have excellent keeping qualities. The vigor and plant habit of this new variety are similar to that of the cultivar Bright Golden Anne and the plant performs as described as a disbud pot plant when flowered during any season at about 42° N. latitude.

I claim:

1. A new and distinct variety of chrysanthemum, substantially as herein shown and described, characterized by the very large size and pure white color of its blooms, its semi-incurve flower form with many broadly spooned ray florets, and its resistance to pinking.

No references cited.

ROBERT E. BAGWILL, Examiner